United States Patent [19]

Witkowski et al.

[11] 3,984,396

[45] *Oct. 5, 1976

[54] 1-(β,-D-RIBOFURANOSYL)-1,2,4-TRIAZOLE ACID ESTERS

[75] Inventors: Joseph T. Witkowski, Laguna Niguel; Roland K. Robins, Santa Ana, both of Calif.

[73] Assignee: ICN Pharmaceuticals, Inc., Irvine, Calif.

[ * ] Notice: The portion of the term of this patent subsequent to Mar. 19, 1991, has been disclaimed.

[22] Filed: Mar. 18, 1974

[21] Appl. No.: 452,065

Related U.S. Application Data

[63] Continuation-in-part of Ser. No. 240,252, March 31, 1972, Pat. No. 3,798,209, which is a continuation-in-part of Ser. No. 149,017, June 1, 1971, abandoned.

[52] U.S. Cl. ............................ 536/23; 424/180; 536/29

[51] Int. Cl.$^2$.......................... C07H 19/04
[58] Field of Search ............... 260/211.5 R

[56] References Cited

UNITED STATES PATENTS

| | | | |
|---|---|---|---|
| 3,798,209 | 3/1974 | Witkowski et al. | 260/211.5 R |
| 3,804,827 | 4/1974 | Robins et al. | 260/211.5 R |

OTHER PUBLICATIONS

Witkowski et al., "J. Org. Chem.," vol. 35, No. 8, 1970, pp. 2635–2639.

*Primary Examiner*—Johnnie R. Brown
*Attorney, Agent, or Firm*—Thomas D. Kiley; Kay H. Boswell

[57] ABSTRACT

Phosphate and carboxylic acid esters of 1-(β-D-ribofuranosyl)-1,2,4-triazoles are prepared by a variety of methods and their antiviral activity reported.

14 Claims, No Drawings

1-($\beta$,-D-RIBOFURANOSYL)-1,2,4-TRIAZOLE ACID ESTERS

CROSS-REFERENCE TO RELATED APPLICATIONS

This is a continuation-in-part of our application Ser. No. 240,252, filed Mar. 31, 1972, which issue as U.S. Pat. No. 3,798,209 on Mar. 19, 1974, which is in turn a continuation-in-part of our application Ser. No. 149,017, filed June 1, 1971 and now abandoned. The disclosure of these applications is expressly incorporated herein by reference.

BACKGROUND AND SUMMARY OF THE INVENTION

In our aforesaid United States applications are described and claimed compounds of structure

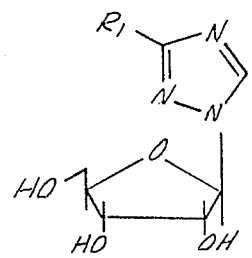

wherein $R_1$ is carboxamido, thiocarboxamido or carboxamidino and its physiologically acceptable acid addition salts, as well as 5'-phosphates and 3',5'-cyclic phosphates thereof, and compounds in which otherwise free glycosyl hydroxyls bear $C_1$-$C_{18}$ acyl groups. The compounds are disclosed in those applications to possess potent antiviral activity. In one embodiment of the present invention, we provide analogous compounds having the same aglycon whose glycosidic moiety is of structure

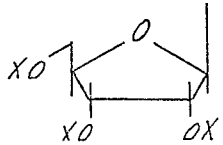

wherein at least one X is $C_1$-$C_{18}$ acyl and at least one X is hydrogen. According to another embodiment of this invention there are provided analogous nucleotides, viz., 2',3'-cyclic phosphates and mixed 2'- and 3'-phosphates of nucleosides of structure (a). Compounds prepared according to this invention exhibit significant antiviral activity in in vivo animal testing, and may be administered generally as in our copending application Ser. No. 340,332, filed Mar. 12, 1973, the disclosure of which is incorporated herein by reference.

DESCRIPTION OF PREFERRED EMBODIMENTS OF THE INVENTION

Preferred 5'-O-acyl compounds are prepared by a variety of methods chosen according to the particular acyl group desired. In the main (Methods 1-3, infra), syntheses of 5'-O-acyl compounds involve isopropylidene blocking of the 2'- and 3' positions, acylation at the 5'-position, and deisopropylidenation. Methods 1 and 2 involve acylation reaction in solvent media (e.g., pyridine) and are employed for the higher molecular weight acyl groups. In Method 1 anhydride reactants are employed, while Method 2 will serve where the corresponding acyl halides are more readily obtainable. Lower molecular weight acyl groups whose corresponding anhydrides are liquid at normal temperatures are attached by Method 3, employing 4-alkylaminopyridine as catalyst. A fourth method of choice, particularly for preparation of 5-O-benzoyl compounds, involves selective deacylation.

Following Examples 1-5 illustrate 5'-O-acylation of the preferred 1-($\beta$-D-ribofuranosyl)-1,2,4-triazole-3-carboxamide. Essentially the same procedures may be employed in forming corresponding 3-thiocarboxamides and 3-carboxamidines, mutatis mutandis.

In each of following Examples (1-3) of preferred embodiments of the invention, the starting material 1-(2,3-O-Isopropylidene-$\beta$-D-ribofuranosyl)-1,2,4-triazole-3-carboxamide was prepared as follows:

1-(2,3-O-Isopropylidene-$\beta$-D-ribofuranosyl)-1,2,4-triazole-3-carboxamide 1-($\beta$-D-Ribofuranosyl)-1,2,4-triazole-3-carboxamide (30.0 g, 123 mole) was suspended in a mixture of acetone (400 ml) and 2,2-dimethoxy-propane (200 ml). The mixture was cooled in an ice bath and 70% perchloric acid (6 ml) was added. The mixture was kept at room temperature for 3 hr and at 5° overnight. The resulting orange solution was neutralized with 2N potassium hydroxide, filtered, and evaporated to dryness. The solid residue was treated with methanol and the insoluble product was removed by filtration. The methanolic solution was concentrated to a small volume and the crystalline product was collected. Recrystallization from a mixture of ethyl-acetate and methanol gave 1-(2,3-O-isopropylidene-$\beta$-D-ribofuranosyl)-1,2,4-triazole-3-carboxamide (31.0 g, 90% with mp 153°–154°.

Anal. Calcd for $C_{11}H_{16}N_4O_5$: C, 46.47; H, 5.67; N, 19.71. Found: C, 46.38; H, 5.73; N, 19.50.

Depending upon the particular 5-O-acyl derivative under preparation, one or more of the following methods was employed.

Method 1. A mixture of 1-(2,3-O-isopropylidene-$\beta$-D-ribofuranosyl)-1,2,4-triazole-3-carboxamide, anhydrous pyridine and the appropriate acyl anhydride is stirred at 60° until the reaction is complete as shown by thin-layer chromatography (24–72 hr). Water is added to the mixture after the reaction is complete and the product is collected by filtration or evaporation and extraction.

The intermediate 1-(5-O-acyl-2,3-O-isopropylidene-$\beta$-D-ribofuranosyl)-1,2,4-triazole-3-carboxamide is converted to the 1-(5-O-acyl-$\beta$-D-ribofuranosyl)-1,2,4-triazole-3-carboxamide by treatment with aqueous acid. A mixture of the isopropylidene intermediate is heated at 100° with a 4:1 (volume/volume) mixture of acetic acid and water until the reaction is complete as shown by thin-layer chromatography (2–5 hr). The solvent is removed by evaporation and the 5-O-acyl product is obtained by crystallization.

Alternatively, the isopropylidene group may be removed from the intermediate 5'-O-acyl-2',3'-O-isopropylidene derivative by treatment with a 9:1 (volume/volume) mixture of trifluoroacetic acid and water at room temperature for 5 min. The reaction mixture is evaporated to dryness and the 5'-O-acyl product is purified by crystallization.

Method 2. A mixture of 1-(2,3-O-isopropylidene-β-D-ribofuranosyl)-1,2,4-triazole-3-carboxamide and anhydrous pyridine is cooled in an ice bath and the appropriate acyl halide is slowly added with stirring. The reaction mixture is kept at room temperature until the reaction is complete as shown by thin-layer chromatography (2-24 hr). Water is added to the mixture and the product is obtained by filtration or evaporation and extraction. The intermediate 1-(5-O-acyl-2,3-O-isopropylidene-β-D-ribofuranosyl)-1,2,4-triazole-3-carboxamide is converted to the 1-(5-O-acyl-β-D-ribofuranosyl)-1,2,4-triazole-3-carboxamide as in Method 1.

Method 3. A mixture of 1-(2,3-O-isopropylidene-β-D-ribofuranosyl)-1,2,4-triazole-3-carboxamide and an excess of the appropriate acyl anhydride containing a catalytic amount (ca. 100 mg) of 4-dimethylaminopyridine is stirred at room temperature until the reaction is complete as shown by thin layer chromatography (16-24 hr). The reaction mixture is evaporated to dryness and the product is isolated and converted to the 1-(5-O-acyl-β-D-ribofuranosyl)-1,2,4-triazole-3-carboxamide as in Method 1. Alternatively, the crude 5'-O-acyl-2',3'-O-isopropylidene product obtained by evaporation may be converted directly without purification to the 1-(5-O-acyl-β-D-ribofuranosyl)-1,2,4-triazole-3-carboxamide by the deisopropylidenation procedures given in Method 1.

Method 4. A mixture of 1-(2,3,5-tri-O-benzoyl-β-D-ribofuranosyl)-1,2,4-triazole-3-carboxylic acid methyl ester and methanol saturated at 0° with anhydrous ammonia was stirred at 0° for 4 hr. The resulting solution was evaporated to dryness under reduced pressure and the product was crystallized from aqueous ethanol to give 1-(5-O-benzoyl-β-D-ribofuranosyl)-1,2,4-triazole-3-carboxamide with mp 182°-184°.

The particular methods employed in preparing the compounds of Example 1-5 appear from Table I, which reports certain of their properties

TABLE 1

Properties of 1-(5-O-Acyl-β-D-ribofuranosyl)-1,2,4-triazole-3-carboxamide

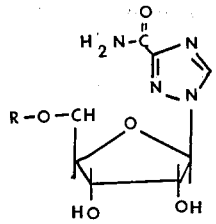

| Example | R | Synthesis | MP (°C) | Empirical Formula | Analyses Calcd - Found | |
|---|---|---|---|---|---|---|
| 1 | CH₃CO— (acetyl) | 3 | 189-190.5 | C₁₀H₁₄N₄O₆ | C 41.96<br>H 4.93<br>N 19.58 | 42.13<br>4.97<br>19.63 |
| 2 | CH₃(CH₂)₂CO— (butyryl) | 3 | 155.5-157 | C₁₂H₁₈N₄O₆ | C 45.85<br>H 5.77<br>N 17.83 | 46.08<br>5.80<br>17.73 |
| 3 | CH₃(CH₂)₁₄CO (Palmitoyl) | 1 | 159-163 | C₂₄H₄₂N₄O₆ | C 59.73<br>H 8.77<br>N 11.61 | 59.81<br>8.80<br>11.63 |
| 4 | ⟨phenyl⟩-CO— (benzoyl) | 2,4 | 182-184 | C₁₅H₁₆N₄O₆ | C 51.72<br>H 4.63<br>N 16.09 | 51.91<br>4.57<br>16.19 |
| 5 | ⟨adamantyl⟩-CO— (adamantoyl) | 2 | amorphous | C₁₉H₂₆N₄O₆ | C 56.14<br>H 6.44<br>N 13.78 | 55.96<br>6.51<br>13.83 |

Of course, compounds within the scope of this invention may be otherwise secured. For example, 5'-O-acyl analogs may be approached via selective acylation, as may be, e.g., 2'-O-acyl, 3'-O-acyl, and di-O-acyl analogs, with consequent separation via column chromatography. See, e.g., C. A. Decker and L. Goodman, *The Carbohydrates*, vol. 2A, p. 26 (2d.ed. 1970) Academic Press, N.Y.

EXAMPLE 6

Various of the compounds prepared in the preceding examples are tested for activity in vivo against Influenza A₂ (Japan 305) induced deaths in male Swiss mice (19-20 gm) and the results compared with those obtained with 1-(β-D-ribofuranosyl)-1,2,4-triazole-3-carboxamide. The mice were intranasally inoculated with virus and treated with compound under test by oral administration twice daily for 8 days commencing 2 hours pre- and 4 hours post-virus inoculation. Virus dosage was 3.2 LD₅₀. Infected mice were observed for 21 days. The results of testing are presented in Table I. All compounds tested were orally non-toxic at the dosages tested.

TABLE I

Effects of Compounds on Influenza $A_2$ (Japan 305)-Induced Deaths in Mice

| Compound of Example | Drug Dose (mg/kg/day) | Infected Survivors Total | Survivor Increase $p^a$ | Mean Survival Time$^b$ (days) | Mean Survival Time Increase $p^c$ |
|---|---|---|---|---|---|
| — | 0 | 1/20 | | 7.1 | |
| * | 75 | 1/10 | 0.46 | 8.0 | <0.05 |
|   | 37.5 | 0/10 | 0.67 | 7.3 | >0.5 |
| 3 | 300 | 0/10 | 0.67 | 8.5 | <0.05 |
|   | 150 | 1/10 | 0.46 | 8.6 | <0.01 |
|   | 75 | 1/10 | 0.46 | 8.2 | <0.01 |
|   | 37.5 | 0/10 | 0.67 | 7.6 | <0.5 |
| 1 | 300 | 1/10 | 0.46 | 8.9 | <0.01 |
|   | 150 | 1/10 | 0.46 | 8.6 | <0.01 |
|   | 75 | 1/10 | 0.46 | 6.7 | — |
|   | 37.5 | 0/10 | 0.67 | 7.3 | >0.5 |
| 2 | 300 | 5/10 | 0.0085 | 9.6 | <0.001 |
|   | 150 | 1/9 | 0.44 | 7.9 | <0.1 |
|   | 75 | 0/10 | 0.67 | 8.0 | <0.05 |
|   | 37.5 | 0/10 | 0.67 | 7.2 | >0.5 |

* 1-($\beta$-D-Ribofuranosyl)-1,2,4-triazole-3-carboxamide
$a_p$=Probability (Fischer Exact Probability Test)
b Animals dying before day 21.
$c_p$=Probability (t test)

The compound of Example 4 was similarly tested, save that the mice were 17–18 g. male Swiss mice, virus dose was 3.2 $LD_{50}$, and drug was first administered 15 minutes prior to virus inoculation.

The results appear in Table II.

TABLE II

Effects of Compounds on Influenza $A_2$ (Japan 305)-Induced Deaths in Mice

| Compound of Example | Drug Dose (mg/kg/day) | Infected Survivors Total | Survivor Increase $p^a$ | Mean Survival Time$^b$ (days) | Mean Survival Time Increase $p^c$ |
|---|---|---|---|---|---|
| * | 75 | 6/10 | <0.05 | 16.5 | <0.01 |
|   | 37.5 | 5/10 | <0.1 | 19.1 | <0.2 |
| 4 | 300 | 8/10 | <0.01 | 18.8 | <0.001 |
|   | 150 | 5/10 | <0.1 | 16.2 | <0.01 |
|   | 75 | 3/10 | >0.3 | 12.5 | >0.3 |
|   | — | 4/20 |  | 11.8 |  |

* 1-($\beta$-D-Ribofuranosyl)-1,2,4-Triazole-3-Carboxamide
$a_p$=Probability (chi square analysis)
b Surviving animals were considered to have died on day 21.
$c_p$=Probability (t test)

The 1-($\beta$-D-ribofuranosyl)-1,2,4-triazole-3-$R_1$ 2',3'-cyclic phosphates of the invention are prepared by an adaptation of the procedure of T. Ueda and I. Kawai, Chem. Pharm. Bull (Japan) 18, 2303 (1970) wherein the corresponding nucleoside is refluxed in dimethylformamide with the tri-n-butyl amine salt of pyrophosphoric acid. Product is purified by cellulose ion exchange chromatography. 5'-O-acyl 2',3'-cyclic phosphates may be similarly prepared, commencing with the 5'-O-acylated nucleosides.

Mixed (2',3') phosphates are secured by cleavage of corresponding cyclic phosphates, as with dilute acid. If desired, otherwise free glycosyl hydroxyls of the resulting mixture may be acylated and O-acyl 2'-and 3'-phosphates separated, one from the other.

EXAMPLE 7

Preparation of 1-$\beta$-D-Ribofuranosyl-1,2,4-triazole-3-carboxamide 2',3'-cyclic phosphate A solution of 1-$\beta$-D-ribofuranosyl-1,2,4-triazole-3-carboxamide (1.22 g., 5.0 mmole), pyrophosphoric acid (10.0 mmole) and tri-n-butyl-amine (40.0 mmole) in dimethylformamide (100 ml) was refluxed for 2.5 hr. The solvent was removed in vacuo and the residue was dissolved in 1N ammonium hydroxide (100 ml). The solution was extracted with ether and the aqueous phase was concentrated to a small volume. The solution was diluted with water to 60 ml and the pH was adjusted to 8.5 with ammonium hydroxide. This solution was applied to a DE 52 cellulose (130 g) column in the bicarbonate form. Elution was with a linear gradient of water (1000 ml) to 0.05 M triethylamine bicarbonate (1000 ml) and fractions of 20 ml were collected. The product was contained in fractions 35–50 which were combined and evaporated to dryness. The residue was dissolved in water (20 ml) and passed through a Dowex 50 × 8 (20 ml) column in the ammonium form. The column was eluted with water and the solution containing the product was evaporated to dryness. The residue was dissolved in methanol and a small amount of impurity was removed by filtration. The filtrate was evaporated to dryness and the residue was dissolved in water. The solution was lyophilized to afford the ammonium salt of the 2',3'-cyclic phosphate.

Anal. Calcd for $C_8H_{14}N_5O_7P.H_2O$: C, 27.93; H, 4.58; N, 21.13. Found: C, 28.16; H, 4.73; N, 20.53.

Alkali metal salts or the free 2',3'-cyclic phosphate may be obtained from the ammonium salt by ion exchange.

After brief treatment with dilute acid the 2',3'-cyclic phosphate was converted to the 2'(3')-phosphate as shown by thin layer chromatography on silica gel with 7:3 (v/v) acetonitrile: 0.1 N aqueous ammonium chloride.

EXAMPLE 8

The compound of Example 7 was tested for antiviral activity by the virus rating (VR) method of Sidwell, et al *Appl. Microbiol* 22, 797 (1971) against type 1 herpes simplex virus (HSV/1), type 13 rhinovirus (RV/13), type 3 parainfluenza virus (PIV/3), influenza virus type A, strain NWS ($1^{NWS}$), and vaccinia virus (VV), in the cell lines shown in Table III below. V.R. > 1.0 is indicative of definite antiviral activity, V.R. of 0.5–0.9 is indicative of moderate antiviral activity, and V.R. < 0.5 suggests slight or no apparent antiviral activity. To demonstrate the antiviral activity of the compounds resulting when the cyclic phosphate was opened by acid hydrolysis, we acidified the solution (in cell culture medium) containing the highest concentration of compound to pH 1.5 with 1N HCl. Formation of a mixture of 1-($\beta$-D-ribofuranosyl)-1,2,4-triazole 2'-and 3'-phosphates was confirmed by thin layer chromatography. This solution and similar solution which has not been acidified were incubated side-by-side at 37°C for 2 hr. The acidified solution was then neutralized by adding 1N NaOH and the two incubated solutions were diluted and tested in cell culture along with a similar solution that had not been incubated.

The resulting VR data follow.

TABLE III

| Compound | Virus Rating of Certain 1,2,4-triazole-3-carboxamide 1-$\beta$-D-Ribotides | | | RV/13 KB | PIV/3 KB | $1^{NWS}$ CE |
|---|---|---|---|---|---|---|
| | KB | RK-13 | KB | | | |
| Ammonium salt of 1-($\beta$-D-ribofuranosyl)-1,2,4-triazole-3-carboxamide 2',3'-cyclic phosphate | 0.8, 1.2 | 1.1 | 0.6 | 0.2, 0.3 | 1.1, 1.1 | 0.4 |
| (incubated) mixed 1-($\beta$-D-ribofuranosyl)-1,2,4-triazole-3-carboxamide 2'- and 3'-phosphates (incubated) | 0.8 | — | — | 0.2 | 1.0 | 0.4 |
| | 0.8 | — | — | 0.6, 0.6 | 1.0 | 0.5 |

The mixture of 2'- and 3'-monophosphates exhibited activity similar to that of the cyclic phosphate, save in the case of RV/13, which proved more sensitive to the non-cyclic phosphates.

We claim:

1. A 1-($\beta$-D-ribofuranosyl)-1,2,4-triazole nucleoside of structure

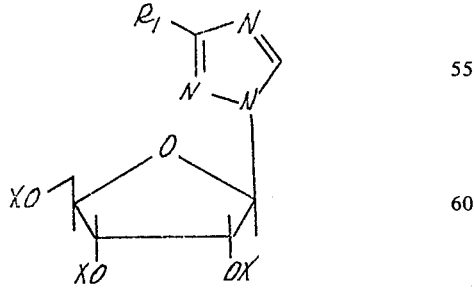

wherein $R_1$ is selected from the group consisting of (a) carboxamido, (b) thiocarboxamido, and (c) carboxamidino groups and physiologically acceptable acid addition salts of (c); and wherein X is hydrogen or $C_1$-$C_{18}$ acyl, at least one X being hydrogen and at least one X being acyl.

2. A 1-(5'-O-acyl-$\beta$-D-ribofuranosyl)-1,2,4-triazole according to claim 1.

3. A compound 1-(5'-O-acyl-$\beta$-D-ribofuranosyl)-1,2,4-triazole-3-carboxamide according to claim 1.

4. A compound 1-(5'-O-acyl-$\beta$-D-ribofuranosyl)-1,2,4-triazole-3-thiocarboxamide according to claim 1.

5. A compound 1-(5'-O-acyl-$\beta$-D-ribofuranosyl)-1,2,4-triazole-3-carboxamidine hydrochloride according to claim 1.

6. 1-(5'-O-Benzoyl-$\beta$-D-ribofuranosyl)-1,2,4-triazole-3-carboxamide.

7. 1-(5'-O-acetyl-$\beta$-D-ribofuranosyl)-1,2,4-triazole-3-carboxamide.

8. 1-(5'-O-butyryl-$\beta$-D-ribofuranosyl)-1,2,4-triazole-3-carboxamide.

9. A 1-($\beta$-D-ribofuranosyl)-1,2,4-triazole nucleotide of structure

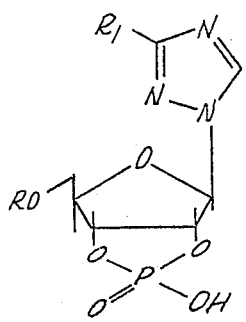

wherein $R_1$ is selected from the group consisting of (a) carboxamido, (b) thiocarboxamido and (c) carboxamidino groups and physiologically acceptable acid addition salts of (c); and wherein R is hydrogen or $C_1$-$C_{18}$ acyl.

10. A compound according to claim 9 wherein R is hydrogen.

11. 1-(β-D-ribofuranosyl)-1,2,4-triazole-3-carboxamide 2′,3′-cyclic phosphate.

12. An hydrolysis product of a compound according to claim 9 comprising a mixture of corresponding 2′- and 3′-monophosphates.

13. A mixture comprising the 2′- and 3′-monophosphates of 1-(β-D-ribofuranosyl)-1,2,4-triazole-3-carboxamide.

14. A compound selected from the group consisting of 2′ and 3′-phosphates of a compound of a structure:

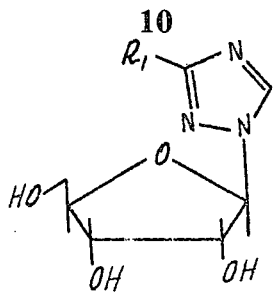

wherein $R_1$ is selected from the group consisting of (a) carboxamido, (b) thiocarboxamido, and (c) carboxamidino groups and physiologically acceptable acid addition salts of (c).

\* \* \* \* \*